(12) United States Patent
Töllner

(10) Patent No.: US 6,319,249 B1
(45) Date of Patent: Nov. 20, 2001

(54) ABLATION SYSTEM

(75) Inventor: Thomas Töllner, Berlin (DE)

(73) Assignee: Biotronik Mess-und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/446,040
(22) PCT Filed: Apr. 14, 1999
(86) PCT No.: PCT/EP99/02515
  § 371 Date: Dec. 15, 1999
  § 102(e) Date: Dec. 15, 1999
(87) PCT Pub. No.: WO99/52461
  PCT Pub. Date: Oct. 21, 1999

(30) Foreign Application Priority Data

Apr. 15, 1998 (DE) ............................................ 198 17 553

(51) Int. Cl.[7] .............................. A61B 18/04; A61B 18/18
(52) U.S. Cl. ................................. 606/34; 606/42; 607/101; 607/102
(58) Field of Search ........................... 606/34, 39, 40–42, 606/45, 49, 50; 607/96–102, 122

(56) References Cited

U.S. PATENT DOCUMENTS

| | | | |
|---|---|---|---|
| 5,472,442 | * 12/1995 | Klicek | 606/42 |
| 5,540,682 | * 7/1996 | Gardner et al. | 606/37 |
| 5,542,916 | * 8/1996 | Hirsch et al. | 604/22 |
| 5,584,830 | 12/1996 | Ladd et al. | |
| 5,680,860 | * 10/1997 | Imran | |
| 5,722,401 | 3/1998 | Pietroski et al. | |
| 6,076,012 | * 6/2000 | SWanson et al. | 604/21 |
| 6,113,596 | * 9/2000 | Hooven et al. | 606/42 |

FOREIGN PATENT DOCUMENTS

| | | |
|---|---|---|
| 90 16 9859 | 4/1991 | (DE) . |
| 0 732 079 | 9/1996 | (EP) . |
| WO 96/00039 | 1/1996 | (WO) . |
| WO 96/32885 | 11/1996 | (WO) . |
| WO 97/20510 | 6/1997 | (WO) . |
| WO 97/33526 | 9/1997 | (WO) . |
| WO 99/52461 | 10/1999 | (WO) . |

OTHER PUBLICATIONS

Mikroprozessoren, Sonderausgabe Elektronik, Franzis–Verlag, München, 1977, S.104; (Linke Sp. "Analog–Ein–/Ausgabesysteme für Mikrocomputer").

* cited by examiner

Primary Examiner—Roy Gibson
(74) Attorney, Agent, or Firm—Venable; Robert Kinberg

(57) ABSTRACT

The invention relates to an ablation system, including an ablation catheter with a plurality of ablation electrodes (34) and a neutral electrode (36), at least one energy source (22), switching elements (26, 28) for connecting the electrodes to the energy source (22) and control elements (16, 18, 20, 24) which are connected to the switching elements (26, 28). The control elements (16, 18, 20, 24) are configured in such a way that electrode pairs made up of both ablation electrodes (34) and an ablation electrode with a neutral electrode (36) can be connected to the energy source (22) in a predetermined sequence. The invention also relates to a method for controlling the electrodes of an ablation system of this type. According to said method, electrode pairs made up of both ablation electrodes (34) and an ablation electrode with a neutral electrode (36) are connected to the energy source (22) in a predetermined sequence.

12 Claims, 3 Drawing Sheets

ABLATION SYSTEM

FIELD OF THE INVENTION

The invention relates to an ablation arrangement which includes an ablation catheter with a plurality of ablation electrodes and a neutral electrode and at least one energy source and switching means for connecting the electrodes to the energy source. The invention also concerns a method of controlling the electrodes of such an ablation arrangement.

BACKGROUND OF THE INVENTION

The term ablation electrode in this respect stands for any small area energy coupling-out element and the term neutral electrode stands for any comparatively large-area energy coupling-out element. In addition the term ablation catheter is used to denote any arrangement of small area energy coupling-out elements which are spatially associated with each other by suitable connecting means.

The invention concerns in particular the general problem of producing line-shaped lesions of sufficient depth throughout in order, for example, to achieve an enduring curative effect in the ablation of tachyarrhythmmia phenomena.

To produce linear lesions of that kind it is known, for example, to use an ablation catheter with a relatively elongated electrode at the free end of the catheter. The linear lesion is produced by the electrode being slowly moved in its longitudinal direction while it is connected to an energy source.

Another ablation arrangement is known from international patent application WO-A97/20510. Described therein is an HF-ablation system in which HF-energy can be delivered simultaneously and in a predetermined phase association by way of a plurality of electrodes of a multipolar catheter. In that case, a number of power modules corresponding to the number of electrodes is used. That arrangement is complicated and expensive due to its structure. In addition, the various electrode systems are not decoupled from each other so that measurement or regulating circuits based thereon have a mutual influencing effect.

SUMMARY OF THE INVENTION

Therefore the object of the present invention is to provide ways and means of producing, in particular, linear ablation without involving high cost.

In accordance with the invention that object is attained by an ablation arrangement which includes control means which are connected to the switching means and which are of such a design that pairs of electrodes formed by two ablation electrodes and also by an ablation electrode together with the neutral electrode can be connected to the energy source in a predeterminable sequence.

In accordance with the invention the object is also attained by a method in which pairs of electrodes are connected to the energy source in a predetermined sequence, wherein the pairs of electrodes are formed both by two ablation electrodes and also by an ablation electrode together with the neutral electrode.

The invention involves the realization that different lesion patterns are formed, depending respectively on whether two ablation electrodes are connected to the energy source or whether one ablation electrode and the neutral electrode are connected to the energy source. An explanation for this phenomenon on which the invention is based is that formed between the corresponding electrodes of a pair thereof is an electrical field which in the region of the small-area ablation electrodes is strongly concentrated and has a high level of energy density while the neutral electrode is of such a large area that the energy density of the field is sufficiently low as not to cause any lesions. In accordance with the invention the result of this is that, upon actuation of a pair of electrodes comprising two ablation electrodes, the lesions occur between those ablation electrodes, while upon actuation of a pair of electrodes consisting of an ablation electrode and the neutral electrode, the lesions occur in the proximity of the one ablation electrode. The lesions can differ for example in terms of their depth: by virtue of the electrical properties of the myocardium to be treated, in comparison with the surrounding blood, the electrical field experiences concentration between two ablation electrodes connected to the energy source, and, depending on the amount of energy, the lesion is of a smaller depth, while the lesions produced by an ablation electrode in conjunction with the neutral electrode have a tendency to extend deeper into the myocardium. Actuation of a pair of electrodes comprising two ablation electrodes is referred to hereinafter as a bipolar mode of operation while actuation of a pair of electrodes consisting of an ablation electrode and the neutral electrode is referred to as a unipolar mode of operation. The core and essence of the invention is to operate an ablation catheter with a plurality of ablation electrodes both in a bipolar and in a unipolar mode in order in that way to produce in particular linear ablations. Accordingly the sequence in which the ablation electrodes are operated, as claimed, includes the unipolar and the bipolar mode of operation of the ablation electrodes.

Preferably the ablation arrangement is designed so that the ablation electrodes are arranged in succession at a determined spacing and the control means are such that the pairs of electrodes formed by two ablation electrodes are formed by mutually adjacent ablation electrodes. In a particularly preferred ablation arrangement, the control means are such that a pair of electrodes formed by ablation electrodes and a pair of electrodes formed by one of the ablation electrodes together the neutral electrode can be connected to the energy source in an alternating maimer. That means, in other words, that respectively adjacent ablation electrodes are used for the bipolar mode of operation and the unipolar and the bipolar modes preferably continuously alternate.

Accordingly, a preferred alternative form of the method is distinguished in that the pairs of electrodes formed by the ablation electrodes are formed by mutually adjacent ablation electrodes of a plurality of ablation electrodes which are disposed in succession at a determined spacing from each other. In a particularly preferred method, a pair of electrodes formed by two ablation electrodes together with the neutral electrode are connected to the energy source in an alternating manner. This also results in alternate unipolar and bipolar operation, in which respect preferably mutually adjacent ablation electrodes are connected to the energy source for the bipolar mode of operation.

A preferred method is also one in which firstly one pair of electrodes is connected to the energy source, which is formed by a first ablation electrode comprising a series of ablation electrodes which occur in succession at a spacing together with the neutral electrode. then a pair of electrodes formed by the first ablation electrode and a second ablation electrode following same, thereupon a pair of electrodes formed by the second ablation electrode and the neutral electrode, thereupon once again a pair of electrodes formed by the second ablation electrode and the next following ablation electrode, and continuing in that way in that alternate sequence, until a desired ablation length is achieved.

When applied to a multipolar catheter with a tip electrode at its free end and a plurality of ring electrodes following the tip electrode, the procedure involved in the method is such that the energy of the energy source is firstly discharged in unipolar fashion between the tip electrode and the neutral electrode, then in bipolar mode between the tip electrode and the first ring electrode, then again in unipolar mode between the first ring electrode and the neutral electrode, then in bipolar mode between the first and second ring electrodes, and so forth, until the desired length of lesion is achieve. The ring electrodes are only referred to by way of example. Instead of ring electrodes, it is also possible for arrays or spirals of electrodes to be actuated in corresponding manner.

A further preferred alternative form of the method is distinguished in that one or more of the ablation electrodes are omitted in the sequence of the electrodes to be connected to the energy source in order to leave gaps in the ablation. This alternative form of the method does not provide a continuous linear ablation, but an ablation which is interrupted.

Another preferred method is one in which the power with which the energy from the energy source is discharged by way of the electrodes is different when a pair of electrodes is formed by two ablation electrodes, from the situation when a pair of electrodes is formed by an ablation electrode together with the neutral electrode. By differentiating between the power for the unipolar mode of operation and the bipolar mode of operation, it is possible for the depth of the lesions produced per ablation in the myocardium to be adapted to each other for the two modes of operation in order to achieve an optimum ablation result.

In general terms, but in particular also in connection with the last mentioned alternative form of the method, a preferred method is one in which the power with which the energy from the energy source is discharged for two ablation electrodes is regulated by measurement of the electrode temperature in such a way that two temperature values which are associated with the two ablation electrodes are taken into consideration for regulation purposes. Taking account of the two temperature values for the two ablation electrodes forming a pair of electrodes can be implemented, for example, by interpolation. Those temperature values may also be incorporated into the power regulation procedure in another fashion.

The above-mentioned ablation arrangement and the method afford on the one hand the advantage that uniform linear lesions can be produced therewith. On the other hand, the spacing of the ablation electrodes from each other on the ablation catheter used can be larger in comparison with conventional ablation catheters. That results in enhanced flexibility of the catheter and thus finer control in regard to positioning.

The further configuration of the ablation arrangement can correspond to that which is described in German patent application No 198 17 553.1.

BRIEF DESCRIPTION OF THE FIGURES

The invention will now be described in greater detail by means of an embodiment with reference to the drawings in which.

DETAILED DESCRIPTION OF THE INVENTION

Figure 1:
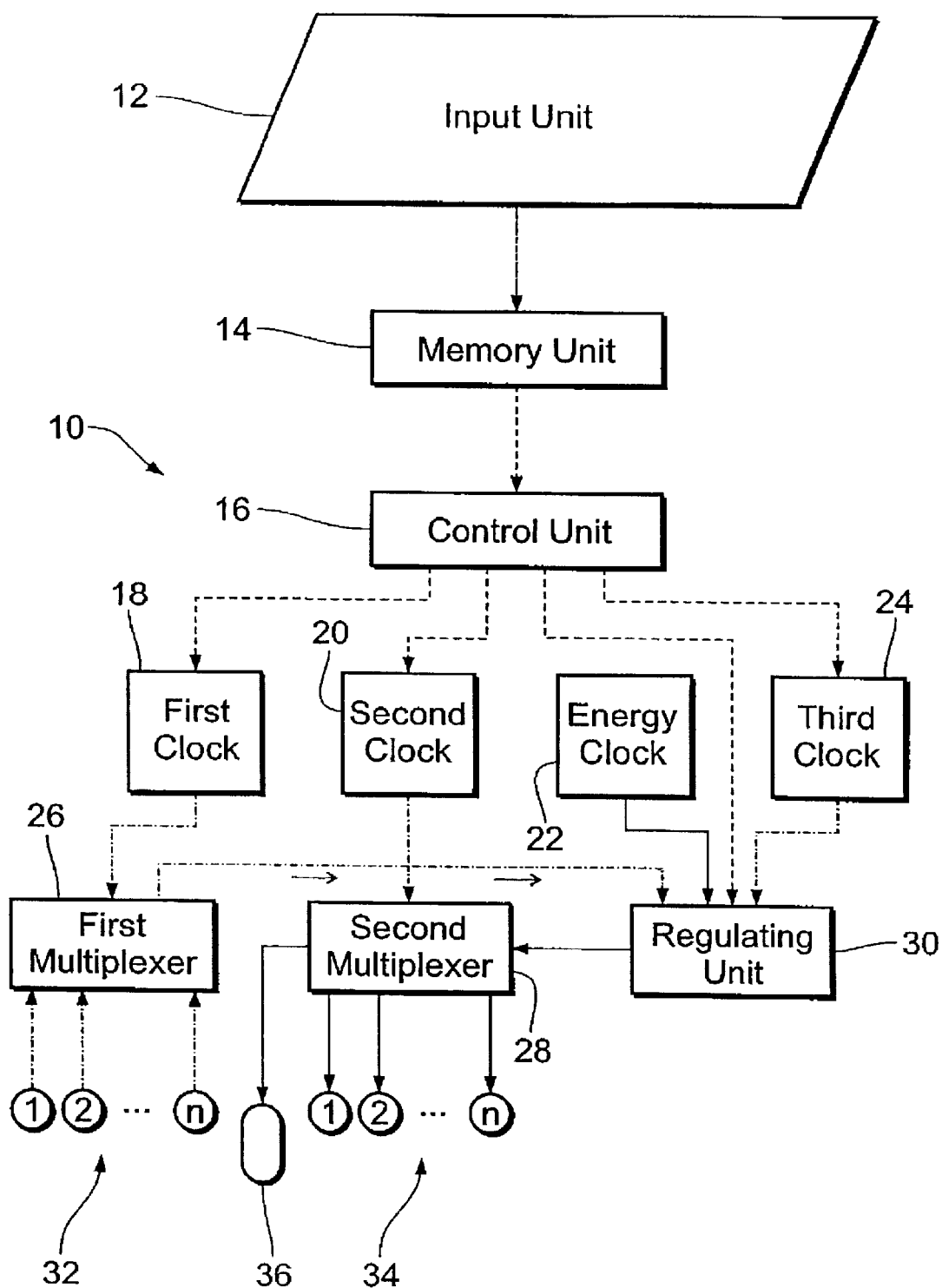
FIG. 1 is a view showing the principle of an ablation arrangement.

FIG. 1 is a view in principle of an ablation arrangement 10 in which the individual components of the ablation arrangement are illustrated in the form of blocks and the connecting lines between the components are shown by broken, dash-dotted and solid lines. The broken lines in that respect identify digital signal lines, the dash-dotted lines denote analog signal lines and the solid lines denote lines for electrical powers. In that respect, the arrows on the lines indicate the direction of flow of the information or electrical currents.

The functional units of the ablation arrangement 10 are an input unit 12. a memory unit 14, a control unit 16, first and second clocks 18 and 20, an energy source 22. a third clock 24, first and second multiplexers 26 and 28, a regulating unit 30, temperature sensors 32, ablation electrodes 34 and finally a surface electrode 36 as a neutral electrode.

In particular for the multiplexer 28 but also for the multiplexer 26, it is possible to use a respective multi-channel power switch which is controlled by the control unit 16. In addition the two multiplexers or power switches can be combined to form a unit.

The input unit 12 serves for parameter input and is connected to the memory unit 14. Parameters to be input are, for example, the number of ablation electrodes 34, the change-over switching frequencies of the multiplexers 26 and 28, the pulse duration for an individual ablation, the ablation power for the unipolar and bipolar modes of operation or the relationship of those power levels in regard to temperature regulation, the maximum ablation temperature and the overall ablation time or the number of ablation sequences. The input parameters are stored in the memory unit 14.

The control unit 16 is connected to the memory unit 14 and has access to the stored parameters by way of a digital signal line connecting the memory unit to the control unit 16. The control unit 16 is connected at its output side by way of digital signal lines to the first, second and third clock generators 18. 20 and 24 and to the regulating unit 30.

The first clock 18 is connected on its output side by way of an analog signal line to the first multiplexer 26. A plurality of temperature sensors 32 are connected to the first multiplexer 26. A plurality of temperature sensors 32 are connected to the first multiplexer by way of analog signal lines. The temperature sensors 32 are, for example, thermocouple elements. In addition the first multiplexer 26 is connected at its output to the regulating unit 30 by way of an analog signal line. The first multiplexer 26, by way of the analog signal lines, respectively transmits to the regulating unit 30 one of the temperature values ascertained by the temperature sensors 32. In that respect, which of the temperature sensors transmits its temperature value to the regulating unit 30 depends on the switching state of the first multiplexer 26.

The second multiplexer 28 is connected at its input side by way of an analog signal line to the second clock 20. In addition, the second multiplexer 28 is connected to the regulating unit 30 by way of an electrical line. On the output side the second multiplexer 28 is connected by way of a respective electrical line to a respective one of the ablation electrodes 34 and to the surface or neutral electrode 36. Depending on its respective switching state, the second multiplexer 28 switches electrical power received from the regulating unit 30, for example in the form of HF-ac voltage, to one of the ablation electrodes 34.

In that respect the switching state of the first multiplexer 26 and the second multiplexer 28 is determined by the first clock 18 and the second clock 20 respectively.

The regulating unit 30 is connected on its input side by way of an electrical line to the energy source 22. The energy source 22 is for example an HF-generator which outputs an electrical ac voltage of a frequency of 470 kHz. The regulating unit 30 is connected at the output side by way of an electrical line to the second multiplexer 28. The regulating unit 30 includes an amplifier and is of such a design that it regulates the power received from the energy source 22 and outputs it controlled by a clock signal received from the third clock 24 and by a control signal received from the control unit 16. For that purpose the regulating unit 30 is connected at its input side by way of a digital signal line to the control unit 16 and by way of an analog signal line to the third clock 24. The regulating unit 30 is further so designed that the power outputted by way of the second multiplexer 28 to two ablation electrodes 34 in the bipolar mode of operation can be different from the power outputted to an ablation electrode and the neutral electrode 36 in the unipolar mode of operation. The power which is delivered to the electrodes 34 and 36 by the regulating unit 30, referred to hereinafter as the ablation power, can also be regulated in dependence on the temperature value received from the first multiplexer 26.

The ablation electrodes 34 are for example the tip electrode and a plurality of ring electrodes of conventional ablation catheters. The temperature sensors 32 are integrated into such an ablation catheter and associated with a respective one of the ablation electrodes 34 of the ablation catheter. The control unit 16 controls the co-operation of the subsequent components of the ablation arrangement 10 in such a way that, to produce a linear ablation, firstly the first of the ablation electrodes (the tip electrode of a per se known ablation catheter) and the neutral electrode 36 are supplied with the high-frequency ac voltage from the energy source 22. In that situation, an electrical field is built up in the body to be treated, between the large-area neutral electrode 36 and the first ablation electrode 34. The ablation electrode 34 is of substantially smaller dimensions than the neutral electrode 36, with the result that the electrical field is concentrated in the region of the ablation electrode 34. That concentration of the electrical field results in an energy density which is sufficient to damage body tissue in the region of the ablation electrode 34, to the desired degree. Then, the first and second of the ablation electrodes 34 are supplied in the bipolar mode of operation with high-frequency electrical energy from the energy source 22. That results in a lesion between the first and second ablation electrodes 34. Thereupon the second of the ablation electrodes 34 is operated in a unipolar mode, that is to say the second of the ablation electrodes 34 and the neutral electrode 36 are supplied with electrical energy from the energy source 22 so that a lesion is produced in the region of the second of the ablation electrodes 34. Then, the second and the third of the ablation electrodes 34 are again supplied in the bipolar mode with high-frequency electrical energy from the energy source 22. Thereupon, the third of the ablation electrodes is again operated in the unipolar mode, that is to say together with the neutral electrode 36. until the length of the lesion produced in that way is sufficient or all ablation electrodes 34 have been operated. A sequence of that kind can be repeated so often until the strength of the lesions suffices. Between the sequential, unipolar discharge of high-frequency ac voltage to the ablation electrodes, adjacent ablation electrodes are briefly operated in a bipolar mode. The ablation catheter is therefore operated alternately in unipolar and bipolar mode. The discharge of electrical energy in the bipolar mode of operation can be reduced or increased in comparison with the unipolar mode in order thereby to control the depth of the lesions.

Therefore, after the discharge of ablation energy in the form of high-frequency ac voltage by way of one of the ablation electrodes 34, before the adjacent ablation electrode is operated in a unipolar mode, high-frequency energy is discharged in a bipolar mode by way of those two adjacent ones of the ablation electrodes 34. The ablation energy supplied can be temperature regulated in dependence on the ablation electrodes. For that purpose, as described, the temperature sensors 32 are respectively disposed in the proximity of one of the ablation electrodes 34. Measurement of the respective ablation electrode temperature is effected by the associated one of the temperature sensors 34 in respective synchronous relationship with the discharge of energy by way of the respective one of the ablation electrodes 34. That synchronicity is achieved by suitable actuation of the first and second multiplexers 26 and 28. The corresponding temperature value is fed to the regulating unit 30 while it regulates the ablation power which is discharged by way of the ablation electrodes and the neutral electrode 36. In that respect, the regulating unit 30 is designed so that differences between the measured temperatures are taken into consideration in regard to the bipolar and the unipolar modes of operation when regulating the ablation power.

Figure 2:
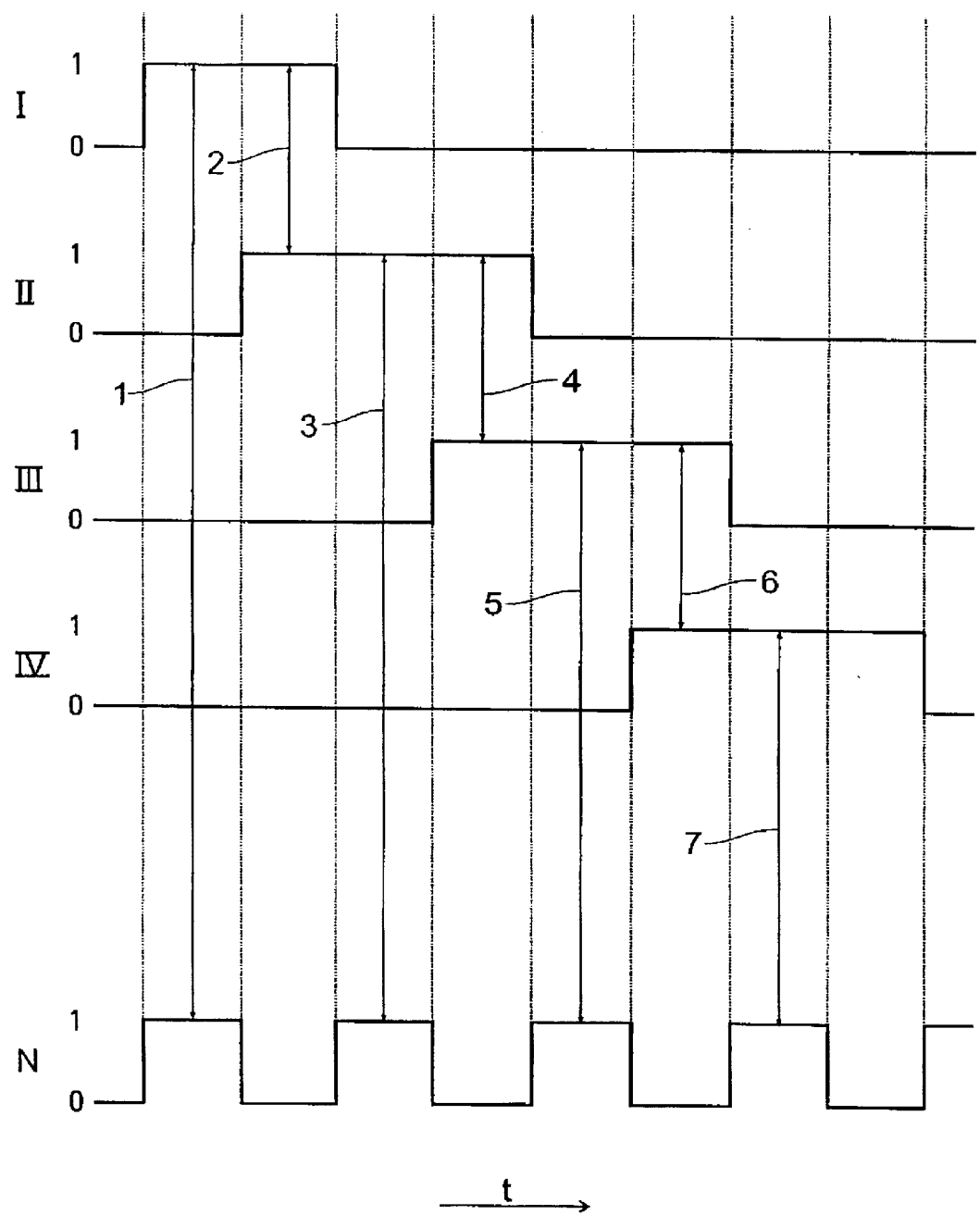
FIG. 2 shows a pulse diagram for the switching states of switching elements which are arranged between the electrodes and the energy source.

The pulse diagram shown in FIG. 2 illustrates how the individual ablation electrodes 34 and the neutral electrode 36 are actuated for the described, strictly alternate unipolar and bipolar mode of operation. In the state identified by "1", the respective electrode is connected to the energy source 22 while in the state identified by "0" it is separated from the energy source 22. The pulse sequence identified by I represents in that respect the state of actuation of the first of the ablation electrodes 34. That will generally be the tip electrode of an ablation catheter. The pulse sequence identified by II represents the actuation state of the next following second ablation electrode, and so forth, while the pulse sequence identified by "N" represents the actuation state of the neutral electrode. The change between the unipolar and bipolar modes is represented by vertical dotted lines. The cycle with which that change takes place is determined by the clocks 18, 20 and 24 which are actuated by the control unit 16. The pulse sequences illustrated in FIG. 2 are plotted in relation to time which progresses from left to right. The arrows 1 through 7 shown in FIG. 2 identify the respectively co-operating electrodes, more specifically arrow 1 identifies the co-operation of the first ablation electrode with the neutral electrode in the unipolar mode, arrow 2 the co-operation of the first and second ablation electrodes in the bipolar mode, arrow 3 the co-operation of the second ablation electrode and the neutral electrode in the unipolar mode, arrow 4 the co-operation of the second and third ablation electrodes in the bipolar mode, arrow 5 the co-operation of the third ablation electrode and the neutral electrode in the unipolar mode, arrow 6 the co-operation of the third and fourth ablation electrodes in the bipolar mode and arrow 7 the co-operation of the fourth ablation electrode and the neutral electrode in the unipolar mode.

The sequence in which the electrodes are actuated can be repeated as often as may be desired until a desired ablation result is achieved. In addition, it is possible for some electrodes in the sequence to be omitted in order to produce lesions which are interrupted.

Figure 3:
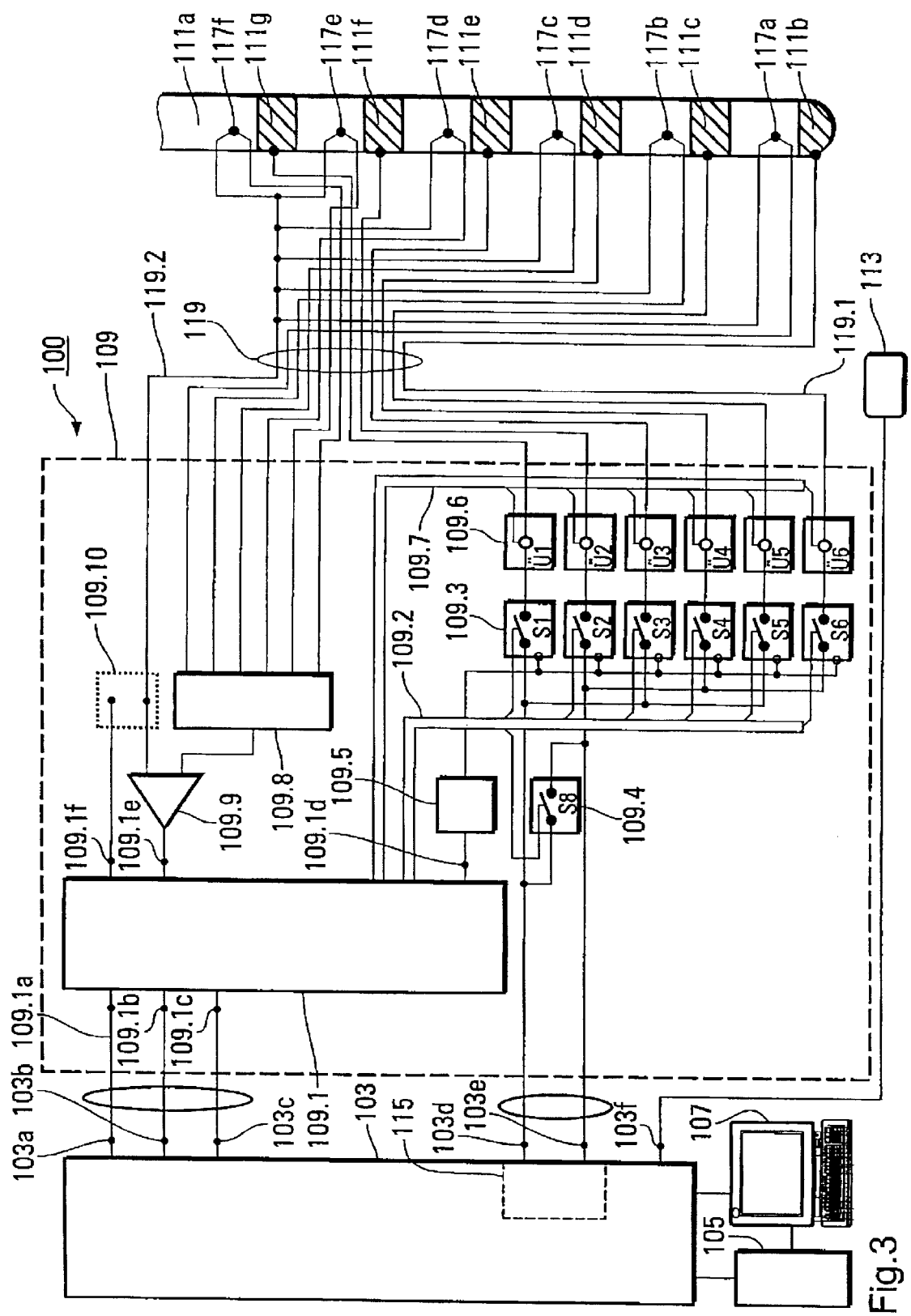
FIG. 3 shows a block circuit diagram of an alternative embodiment of the ablation arrangement.

FIG. 3 shows a block circuit diagram of an embodiment of the ablation arrangement, showing alternatives in parts thereof. The ablation arrangement 100 shown in FIG. 3 comprises the components ablation device 103, stimulation device 105, clinical measuring station 107, switching device 109, multipolar ablation catheter 111 and surface electrode 113 which co-operate in known manner. In that respect, in regard to describing the invention, the ablation device 103, the HF-generator 115 and the output terminals are of particular interest. There are two serial data terminals 103a, 103b, a power supply terminal 103c, an HF-power output 103d, 103e and a reference terminal 103f for the surface electrode 113.

The ablation catheter 111 is also of per se known type and, on an insulating catheter body 111a made from a biocompatible plastic material, besides a tip or point electrode 111b, has five ring electrodes 111c through 111g which are arranged equidistantly relative to each other and in relation to the tip electrode and which—like the tip electrode 111a—are preferably made from platinum or a Pt—Ir-alloy and together with the tip electrode form the ablation electrodes. The catheter body 111a accommodates feed lines (not individually shown) for the individual electrodes and the constantan or copper wires (also not individually shown) for thermocouple elements 117a through 117f spatially associated with the electrodes. HF-lines 119.1 and the temperature signal lines 119.2 are guided in a connecting line 119 from the switching device 109 to the ablation catheter 111.

The switching device is connected on its input side (by lines which once again are not shown specifically) to the output terminals 115a to 115e of the ablation device. As the most important components for ablation control it includes a microcontroller 109.1, six electronic switches 109.3 connected to the microcontroller by way of a bus line 109.2 for the catheter electrodes 111b through 111g and a safety cut-out switch 109.f and finally a watchdog timer 109.5. Associated with the HF-output lines 119.1 are current monitoring sensors 109.6 which are connected to the microcontroller 109.1 by way of a second bus line 109.7.

The microcontroller is connected by way of data inputs and outputs 109.1a, 109.1b to the data inputs and outputs 103a, 103b of the ablation device and by way of a current supply input 109.1c to the current supply output 103.c thereof, while a separate control output 109.1d is provided for the watchdog timer 109.5.

The Cu-lines of the thermocouple elements 117a through 117f are connected by way of a multiplexer 109.8 and the constantan line directly to a single measuring amplifier 109.9, and the output thereof is connected to a first T-signal input 109.1d of the microcontroller. A cold junction 109.10 serving as a reference with a thermistor (not shown) for T-detection is connected directly to a second T-signal input 109.1e of the microcontroller.

The primary control functions for an ablation treatment (choice of electrode and sequence of electrode actuation, duration and spacings of the HF-pulses and so forth) are implemented after evaluation of the results, obtained by means of the measuring station 107, of the clinical investigation, on the basis of a suitable programming, by the doctor, in the ablation device 103 (which in practice is also referred to as an ablator or ablation system). The ablation device 103 is of such a design configuration that the ablation electrodes are operated both in unipolar and in bipolar mode within a sequence and that the ablation power for the unipolar mode is different than from the bipolar mode. Control commands for the ablation device are fed by way of the data outputs 103a, 103b to the microcontroller 109.1 which inter alia converts the control commands into control signals for the switches 109.3 and the multiplexer 109.9 which monitors switching functions by means of the current sensors 109.6 and calculates the temperature at the individual electrodes 117a through 117f.

The illustrated switch arrangement makes it possible to discharge HF-energy with any desired combination of ablation electrodes with each other or with the surface or neutral electrode 113 and the application of stimulation pulses and the detection of an intracardial electrogram IEGM at the electrodes which are respectively switched on. At the same time, by virtue of synchronous control of the multiplexer 109.8, it is possible to monitor the temperature at the electrodes, but if necessary the multiplexer can also be controlled in an asynchronous relationship with the switches. The results of T-monitoring are transmitted to the ablation device 103 to be displayed for the doctor and for any modification to the ablation program, but they can also be used internally in the microcontroller 109.1 for triggering an electrode switch-off procedure in the event of unacceptably high T-values.

The switches 109.3 and 109.4 are preferably in the form of MOSFET-switches but—if the limitation in change-over switching speed is acceptable—they can also be formed by relays. The bidirectional transmission of data between the ablator 103 and the switching device 109 or suitable programming of the ablator permits short-term blanking out of the HF at each electrode change-over switching operation in order to reduce the switch loading, which is advantageous in particular when using the relays.

What is claimed is:

1. In an ablation catheter having at least three of ablation electrodes and a neutral electrode, a method of actuating electrodes, comprising:

providing an energy source; and connecting pairs of electrodes formed by the plurality of ablation electrodes and pairs of electrodes formed by the neutral electrode and one of the ablation electrodes to the energy source in a predetermined sequence.

2. The method of claim 1, wherein the ablation electrodes are arranged in a series one after the other with a spacing in between and the pairs of electrodes formed by the ablation electrodes are formed from adjacent ablation electrodes.

3. The method of claim 1, wherein the predetermined sequence spefices connecting a pair of electrodes formed by the ablation electrodes and a pair of electrodes formed by the neutral electrode and one of ablation electrodes to the energy source in an alternating manner.

4. The method of claim 2, wherein the connecting step further comprises:

a) connecting a pair of electrodes formed by a first one of the ablation electrodes in the series and the neutral electrode to the energy source;

b) connecting a pair of electrodes formed by the first one of the ablation electrode in the series and the next ablation electrode in the series to the energy source;

c) connecting a pair of electrodes formed by the next ablation electrodes in the series and the neutral electrode to the energy source;

d) connecting a pair of electrodes formed from the next adjacent ablation electrodes to the energy source; and e) repeating steps c)-d) until a desired ablation length is reached.

5. The method of claim 2, further comprising omitting connecting one of the ablation electrodes in the series to the energy source to create an ablation gap.

6. The method of claim 1, further comprising:

providing a first amount of power from the energy source when the pair of electrodes is formed by two ablation electrodes; and providing a second amount of power from the energy source when the pair of electrodes is formed by the neutral electrode and one of the ablation electrodes.

7. The method of claim 1, further comprising:

measuring temperatures of the ablation electrodes connected to the energy source; and determining an amount of power supplied to the ablation electrodes from the energy source based on the measured temperature.

8. An ablation apparatus, comprising:

at least three of ablation electrodes;

a neutral electrode;

an energy source;

switching elements for connecting the ablation electrodes and the neutral electrode to the energy source;

control means connected to the switching elements to connect pairs of electrodes formed by (a) the ablation electrodes, and (b) by the neutral electrode and one of the ablation electrodes to the energy source in a predetermined sequence.

9. The ablation apparatus of claim 8, wherein the ablation electrodes are arranged one after the other in a series, and the pairs of electrodes formed by the ablation electrodes are formed by adjacent ablation electrodes.

10. The ablation apparatus of claim 8, wherein the control means connects a pair of electrodes formed by the ablation electrodes and a pair of electrodes formed by the neutral electrode and one of ablation electrodes to the energy source in an alternating manner.

11. In an ablation apparatus including a neutral electrode and a plurality of ablation electrodes arranged in a series one after the other with spacing therebetween, a method of activating the electrodes, comprising:

alternately operating the ablation electrodes, proceeding in order down the series, in a unipolar and bipolar mode.

12. The method of claim 11, wherein adjacent ablation electrodes are connected to an energy source in the bipolar mode.

* * * * *